United States Patent
DeKeyser (10) Patent No.: US 7,243,440 B2
(45) Date of Patent: Jul. 17, 2007

(54) GAUGE FOR USE WITH POWER TOOLS

(75) Inventor: Kathy DeKeyser, Jackson, TN (US)

(73) Assignee: Black & Decker Inc., Newark, DE (US)

( * ) Notice: Subject to any disclaimer, the term of this patent is extended or adjusted under 35 U.S.C. 154(b) by 0 days.

(21) Appl. No.: 10/959,413

(22) Filed: Oct. 6, 2004

(65) Prior Publication Data

US 2006/0112580 A1    Jun. 1, 2006

(51) Int. Cl.
*B23B 49/00*   (2006.01)

(52) U.S. Cl. .............................. 33/626; 33/833; 33/638; 175/45; 433/27; 408/8; 408/16

(58) Field of Classification Search .................. 33/613, 33/645, 626, 632, 638, 640; 408/8, 16; 433/27; 175/40, 45
See application file for complete search history.

(56) References Cited

U.S. PATENT DOCUMENTS

| | | |
|---|---|---|
| 299,619 A | 6/1884 | Carson |
| 408,790 A | 8/1889 | Butler |
| 411,925 A | 10/1889 | Linderman |
| 714,098 A | 11/1902 | Caldwell |
| 1,476,238 A | 12/1923 | Bump |
| 1,804,764 A | 5/1931 | Grant |
| 2,109,976 A | 3/1938 | Pierce, Jr. ................... 177/311 |
| 2,121,069 A | 6/1938 | Collins ........................ 143/36 |
| 2,146,906 A | 2/1939 | Moller ............................ 77/5 |
| 2,299,262 A | 10/1942 | Uremovich .................. 143/36 |
| 2,307,820 A | 1/1943 | Butters ........................ 143/168 |
| 2,357,194 A | 8/1944 | Hazelton et al. .............. 164/47 |
| 2,407,845 A | 9/1946 | Nemeyer ..................... 116/124 |
| 2,465,000 A | 3/1949 | Turner ........................ 143/132 |
| 2,488,947 A | 11/1949 | Vavrik .......................... 143/43 |
| 2,518,684 A | 8/1950 | Harris .......................... 143/45 |
| 2,557,029 A | 6/1951 | Griffin ........................... 88/39 |
| 2,806,492 A | 9/1957 | Becker ....................... 143/168 |
| 2,850,054 A | 9/1958 | Eschenburg ................. 143/36 |
| 2,855,679 A | 10/1958 | Gibble .......................... 33/46 |

(Continued)

FOREIGN PATENT DOCUMENTS

CN    2378150 Y    5/2000

(Continued)

OTHER PUBLICATIONS

"Instruction Manual Redeye® 1800W 184mm (7 1/4") Circular Saw with Laser Line Generator, Model LS5000 ," GMC Global Machinery Company, 45-55 South Centre Road, Melbourne Airport, Victoria 3045, Australia; 14 pages.

(Continued)

*Primary Examiner*—Yaritza Guadalupe-McCall
(74) *Attorney, Agent, or Firm*—Scott B. Markow (57) ABSTRACT

A gauge for connecting with a power tool and providing a system for determining structural factors of a workpiece to be operated upon by the power tool is provided by the present invention. The gauge including a probe connected with a sensor via a spring, wherein contact by the probe with the workpiece allows a reading by the sensor which may be utilized to determine the proper operational settings of the power tool based on the determined structural factors of the workpiece.

27 Claims, 8 Drawing Sheets

U.S. PATENT DOCUMENTS

| | | | |
|---|---|---|---|
| 3,005,477 A | 10/1961 | Sherwen | 143/47 |
| 3,011,529 A | 12/1961 | Copp | 143/36 |
| 3,013,592 A | 12/1961 | Ambrosio et al. | 143/36 |
| 3,124,178 A | 3/1964 | Packard | 143/36 |
| 3,179,458 A | 4/1965 | Sconzo | 292/341.15 |
| 3,344,819 A | 10/1967 | Mitchell | 143/36 |
| 3,529,467 A | 9/1970 | Townend | |
| 3,572,937 A | 3/1971 | Baldwin | 356/110 |
| 3,597,091 A | 8/1971 | Bowker | 356/106 |
| 3,635,108 A | 1/1972 | Prince | 82/1 |
| 3,713,746 A | 1/1973 | Luthy | 408/8 |
| 3,728,027 A | 4/1973 | Watanabe | 356/13 |
| 3,780,777 A | 12/1973 | Davies | 144/3 N |
| 3,837,757 A | 9/1974 | Levine | 408/14 |
| 3,854,836 A | 12/1974 | Weissman | 408/14 |
| 3,891,039 A | 6/1975 | Lagerstrom | 175/40 |
| 3,970,359 A | 7/1976 | Starkweather | 350/7 |
| 3,972,582 A | 8/1976 | Oosaka et al. | 350/7 |
| 3,976,384 A | 8/1976 | Matthews et al. | 356/200 |
| 4,046,985 A | 9/1977 | Gates | 219/121 L |
| 4,078,869 A | 3/1978 | Honeycutt | 408/16 |
| 4,184,394 A | 1/1980 | Gjerde | 83/477.1 |
| 4,255,056 A | 3/1981 | Peterson | 356/401 |
| 4,257,297 A | 3/1981 | Nidbella | 83/471.3 |
| 4,319,403 A | 3/1982 | Stearns | 33/185 R |
| 4,338,723 A | 7/1982 | Benjamin | 33/174 L |
| 4,383,373 A | 5/1983 | Couturier | 33/286 |
| 4,386,532 A | 6/1983 | Benjamin | 73/862.04 |
| 4,413,662 A | 11/1983 | Gregoire et al. | 144/356 |
| 4,438,567 A | 3/1984 | Raiha | 33/286 |
| 4,447,956 A | 5/1984 | Chung | 33/172 D |
| 4,450,627 A | 5/1984 | Morimoto | 30/391 |
| 4,468,992 A | 9/1984 | McGeehee | 83/56 |
| 4,469,318 A | 9/1984 | Slavic | 269/91 |
| 4,469,931 A | 9/1984 | Macken | 219/121 LG |
| 4,503,740 A | 3/1985 | Brand et al. | 83/521 |
| 4,534,093 A | 8/1985 | Jahnke et al. | 29/26 A |
| 4,566,202 A | 1/1986 | Hamar | 33/286 |
| 4,581,808 A | 4/1986 | Lawson et al. | 29/558 |
| 4,589,208 A | 5/1986 | Iwasaki et al. | 30/376 |
| 4,598,481 A | 7/1986 | Donahue | 33/288 |
| 4,607,555 A | 8/1986 | Erhard | 83/471.2 |
| 4,651,732 A | 3/1987 | Frederick | 128/303 R |
| 4,676,130 A | 6/1987 | Nutt | 83/155 |
| 4,723,911 A | 2/1988 | Kurtz | 433/27 |
| 4,725,933 A | 2/1988 | Houk | 362/287 |
| 4,775,205 A | 10/1988 | Muramatsu | 350/6.8 |
| 4,803,976 A | 2/1989 | Frigg et al. | 128/92 |
| 4,805,500 A | 2/1989 | Saito et al. | 83/277 |
| 4,817,839 A | 4/1989 | Weissman | 225/2 |
| 4,820,911 A | 4/1989 | Arackellian et al. | 235/467 |
| 4,833,782 A | 5/1989 | Smith | 30/392 |
| 4,836,671 A | 6/1989 | Bautista | 356/1 |
| 4,885,965 A | 12/1989 | Veissman | 83/100 |
| 4,885,967 A | 12/1989 | Bell et al. | 83/520 |
| 4,887,193 A | 12/1989 | Dieckmann | 362/89 |
| 4,934,233 A | 6/1990 | Brundage et al. | 83/397 |
| 4,945,797 A | 8/1990 | Hahn | 83/75.5 |
| 4,964,449 A | 10/1990 | Conners | 144/286 R |
| 4,976,019 A | 12/1990 | Kitamura | 29/26 A |
| 4,978,246 A | 12/1990 | Quenzi et al. | 404/84 |
| 5,013,317 A | 5/1991 | Cole et al. | 606/96 |
| 5,031,203 A | 7/1991 | Trecha | 378/205 |
| 5,038,481 A | 8/1991 | Smith | 30/392 |
| 5,052,112 A | 10/1991 | MacDonald | 33/263 |
| 5,066,176 A * | 11/1991 | Johnstone | 33/638 |
| 5,146,232 A | 9/1992 | Duey et al. | 356/152 |
| 5,159,864 A | 11/1992 | Wedemeyer et al. | 83/13 |
| 5,159,869 A | 11/1992 | Tagliaferri | 83/862 |
| 5,161,922 A | 11/1992 | Malloy | 408/14 |
| 5,203,650 A | 4/1993 | McCourtney | 408/1 R |
| 5,207,007 A | 5/1993 | Cucinotta et al. | 33/640 |
| 5,212,720 A | 5/1993 | Landi et al. | 378/206 |
| 5,267,129 A | 11/1993 | Anderson | 362/96 |
| 5,283,808 A | 2/1994 | Cramer et al. | 378/206 |
| 5,285,708 A | 2/1994 | Bosten et al. | 83/520 |
| 5,316,014 A | 5/1994 | Livingston | 128/754 |
| 5,320,111 A | 6/1994 | Livingston | 128/754 |
| 5,357,834 A | 10/1994 | Ito et al. | 83/471.3 |
| 5,365,822 A | 11/1994 | Stapleton et al. | 83/745 |
| 5,375,495 A | 12/1994 | Bosten et al. | 83/520 |
| 5,387,969 A | 2/1995 | Marantette | 356/4.5 |
| 5,426,687 A | 6/1995 | Goodall et al. | 378/206 |
| 5,439,328 A | 8/1995 | Haggerty et al. | 408/1 R |
| 5,446,635 A | 8/1995 | Jehn | 362/259 |
| 5,461,790 A | 10/1995 | Olstowski | 30/391 |
| 5,481,466 A | 1/1996 | Carey | 364/474.09 |
| 5,488,781 A | 2/1996 | Van Der Horst | 33/617 |
| 5,495,784 A | 3/1996 | Chen | 83/471.2 |
| 5,522,683 A | 6/1996 | Kakimoto et al. | 408/13 |
| 5,529,441 A | 6/1996 | Kosmowski et al. | 408/1 R |
| 5,546,840 A | 8/1996 | Supe-Dienes | 83/478 |
| 5,579,102 A | 11/1996 | Pratt et al. | 356/3.12 |
| 5,593,606 A | 1/1997 | Owen et al. | 219/121.71 |
| 5,644,616 A | 7/1997 | Landi et al. | 378/206 |
| 5,661,775 A | 8/1997 | Cramer et al. | 378/206 |
| 5,662,017 A | 9/1997 | Mellon | 83/169 |
| 5,667,345 A | 9/1997 | Wiklund | 408/1 R |
| 5,675,899 A | 10/1997 | Webb | 30/390 |
| 5,720,213 A | 2/1998 | Sberveglieri | 83/471.3 |
| 5,741,096 A | 4/1998 | Olds | 408/1 R |
| 5,777,562 A | 7/1998 | Hoffman | 340/870.07 |
| 5,782,842 A | 7/1998 | Kloess et al. | 606/130 |
| 5,784,792 A | 7/1998 | Smith | 33/227 |
| 5,797,670 A | 8/1998 | Snoke et al. | 362/119 |
| 5,819,625 A | 10/1998 | Sberveglieri | 83/471.3 |
| 5,835,517 A | 11/1998 | Jayaraman et al. | 372/50 |
| 5,835,519 A | 11/1998 | Tsukamoto et al. | 372/55 |
| 5,862,727 A | 1/1999 | Kelly | 83/13 |
| 5,879,312 A | 3/1999 | Imoto | |
| 5,911,482 A | 6/1999 | Campbell et al. | 30/390 |
| 5,918,523 A | 7/1999 | Cutter | 83/520 |
| 5,943,931 A | 8/1999 | Stumpf et al. | 83/468.2 |
| 5,943,932 A | 8/1999 | Sberveglieri | 83/471.3 |
| 5,949,810 A | 9/1999 | Star et al. | 372/108 |
| 5,968,383 A | 10/1999 | Yamazaki et al. | 219/121.75 |
| 5,979,523 A | 11/1999 | Puzio et al. | 144/286.5 |
| 5,995,230 A | 11/1999 | Madlener et al. | 356/375 |
| 5,996,460 A | 12/1999 | Waite | 83/520 |
| 6,023,071 A | 2/2000 | Ogura et al. | 250/586 |
| 6,035,757 A | 3/2000 | Caluori et al. | 83/520 |
| 6,076,445 A | 6/2000 | Kenyon et al. | 83/477.2 |
| 6,137,577 A | 10/2000 | Woodworth | 356/376 |
| 6,152,372 A | 11/2000 | Colley et al. | 235/472.01 |
| 6,209,597 B1 | 4/2001 | Calcote | 144/326 |
| 6,223,794 B1 | 5/2001 | Jones | 144/135.2 |
| 6,239,913 B1 | 5/2001 | Tanaka | 359/619 |
| 6,263,584 B1 | 7/2001 | Owens | 33/640 |
| 6,283,002 B1 | 9/2001 | Chiang | 83/477.1 |
| 6,290,437 B1 | 9/2001 | Mattheck et al. | |
| 6,301,997 B1 | 10/2001 | Welte | 81/54 |
| 6,328,505 B1 | 12/2001 | Gibble | 408/16 |
| 6,375,395 B1 | 4/2002 | Heintzeman | 408/16 |
| 6,413,022 B1 | 7/2002 | Sarh | 408/76 |
| 6,419,426 B1 | 7/2002 | Chalupa et al. | 408/1 R |
| 6,460,768 B2 | 10/2002 | Ring et al. | 235/462.43 |
| D465,165 S | 11/2002 | Doyle et al. | D10/65 |
| 6,493,955 B1 | 12/2002 | Moretti | 33/451 |
| 6,494,590 B1 | 12/2002 | Paganini et al. | 362/119 |
| 6,530,303 B1 | 3/2003 | Parks et al. | 83/473 |
| 6,536,536 B1 | 3/2003 | Gass et al. | 173/2 |
| 6,546,835 B2 | 4/2003 | Wang | 83/477.1 |
| 6,550,118 B2 | 4/2003 | Smith et al. | 29/26 A |
| 6,565,227 B1 | 5/2003 | Davis | 362/119 |

| | | | | | |
|---|---|---|---|---|---|
| 6,584,695 B1 | 7/2003 | Chang .................... 30/391 | JP | 2001-157951 | 6/2001 |
| 6,587,184 B2 | 7/2003 | Wursch et al. ............ 356/4.01 | JP | 2001-158003 | 6/2001 |
| 6,593,587 B2 | 7/2003 | Pease ................. 250/559.19 | JP | 2001-300818 | 10/2001 |
| 6,621,565 B2 | 9/2003 | Pratt et al. ............... 356/141.4 | JP | 2001-300902 | 10/2001 |
| 6,644,156 B2 | 11/2003 | Villacis ....................... 83/425 | JP | 2001-347501 | 12/2001 |
| 6,647,868 B2 | 11/2003 | Chen ........................... 100/99 | TW | 537083 | 12/1990 |
| 6,662,457 B2 | 12/2003 | Dameron .................... 33/286 | TW | 517615 | 5/1991 |
| 6,665,948 B1* | 12/2003 | Kozin et al. .................. 33/833 | TW | 411888 | 11/2000 |
| 6,684,750 B2 | 2/2004 | Yu .............................. 83/473 | | | |
| 6,688,203 B2 | 2/2004 | Chen .......................... 83/520 | | | |
| 6,736,042 B2 | 5/2004 | Behne et al. ............. 83/440.2 | | | |
| 6,736,044 B2 | 5/2004 | Chang ........................ 83/473 | | | |
| 6,739,042 B2 | 5/2004 | Thorum ..................... 29/832 | | | |
| 6,763,597 B2 | 7/2004 | Lysen ......................... 33/286 | | | |
| 6,813,843 B1* | 11/2004 | Faubion ...................... 33/638 | | | |
| 6,832,440 B2* | 12/2004 | Navarro et al. ............. 33/638 | | | |
| 6,925,725 B2* | 8/2005 | Herrmann et al. ........... 33/638 | | | |
| 2001/0028025 A1 | 10/2001 | Pease ..................... 250/208.1 | | | |
| 2001/0029819 A1 | 10/2001 | Okouchi ........................ 83/13 | | | |
| 2001/0034951 A1 | 11/2001 | Sears .......................... 33/640 | | | |
| 2001/0049988 A1 | 12/2001 | Ushiwata et al. ............. 83/520 | | | |
| 2002/0000148 A1 | 1/2002 | Brun .......................... 83/520 | | | |
| 2002/0054491 A1 | 5/2002 | Casas ........................ 362/109 | | | |
| 2002/0054798 A1* | 5/2002 | Dils et al. ................... 408/124 | | | |
| 2002/0059871 A1 | 5/2002 | Chen ........................... 100/35 | | | |
| 2002/0131267 A1 | 9/2002 | Van Osenbruggen ....... 362/109 | | | |
| 2002/0146295 A1 | 10/2002 | Schaer et al. ................. 408/16 | | | |
| 2002/0164217 A1 | 11/2002 | Peterson ..................... 408/1 R | | | |
| 2002/0170404 A1 | 11/2002 | Peot et al. ..................... 83/478 | | | |
| 2003/0000355 A1 | 1/2003 | Butler et al. ................... 83/13 | | | |
| 2003/0010173 A1 | 1/2003 | Hayden ...................... 83/520 | | | |
| 2003/0016085 A1 | 1/2003 | Wursch et al. | | | |
| 2003/0027353 A1 | 2/2003 | Bright et al. ............... 436/173 | | | |
| 2003/0029050 A1 | 2/2003 | Fung et al. ................... 33/626 | | | |
| 2003/0101857 A1 | 6/2003 | Chuang ..................... 83/477.1 | | | |
| 2003/0150312 A1 | 8/2003 | Chang ........................ 83/473 | | | |
| 2003/0197138 A1 | 10/2003 | Pease et al. ............ 250/559.19 | | | |
| 2003/0200851 A1 | 10/2003 | Yu ............................. 83/471.3 | | | |
| 2003/0209678 A1 | 11/2003 | Pease .................... 250/559.19 | | | |
| 2003/0233921 A1 | 12/2003 | Garcia et al. ................. 83/520 | | | |
| 2004/0032587 A1 | 2/2004 | Garcia et al. ............... 356/399 | | | |

FOREIGN PATENT DOCUMENTS

| | | |
|---|---|---|
| CN | 2508922 Y | 9/2002 |
| CN | 2528568 Y | 1/2003 |
| CN | 2546122 Y | 4/2003 |
| DE | 2838968 | 3/1980 |
| DE | 3324428 | 1/1984 |
| DE | 3333428 | 4/1985 |
| DE | 3918070 | 12/1990 |
| DE | 40 04 242 A1 | 8/1991 |
| DE | 4435573 | 4/1996 |
| DE | 19819332 | 11/1998 |
| DE | 19907880 | 8/2000 |
| DE | 10037532 | 2/2001 |
| DE | 102 07 566 A1 | 9/2003 |
| EP | 0366039 | 5/1990 |
| EP | 0504745 | 3/1991 |
| JP | 55125954 | 9/1980 |
| JP | 61061705 | 3/1986 |
| JP | 61131246 | 6/1986 |
| JP | 61159312 | 7/1986 |
| JP | 62166914 | 7/1987 |
| JP | 62274738 | 11/1987 |
| JP | 63162143 | 7/1988 |
| JP | 08197381 | 8/1996 |
| JP | 10-109253 | 4/1998 |
| JP | 11-170203 | 6/1999 |
| JP | 200-225603 | 8/2000 |
| JP | 2000-225602 | 8/2000 |
| JP | 2000-317901 | 11/2000 |
| JP | 2001-150401 | 6/2001 |

OTHER PUBLICATIONS

"Instruction Manual Redeye® 305mm (12") Compound Mitre Saw with Laser Line Generator, Model LMS305 ," GMC Global Machinery Company, 45-55 South Centre Road, Melbourne Airport, Victoria 3045, Australia; 19 pages.

"Instruction Manual Redeye® 2000W 250mm (10") Table Saw with Laser Line Generator, Model LS250TS," GMC Global Machinery Company, 45-55 South Centre Road, Melbourne Airport, Victoria 3045, Australia; 20 pages.

"Product Picks from the National Hardware Show"; Fall Homes 1992; Sep. 23, 1992; 2 pages.

"Delta, Building Trades and Home Shop Machinery"; Catalog published in Jan. 1993; (see generally pp. 5-25), 84 pages.

Craftsman Operator's Manual, "Laser Compound Miter Saw with Retractable Laser Trac® System, Model No. 137.212540," Part No. 137212540001; Sears, Roebuck and Co., Hoffman Estates, IL 60179; www.sears.com/craftsman; © Sears, Roebuck and Co.; 34 pages.

"Hitachi Model C 10FSH and C 10FSB Slide Compound Saw, Safety Instructions and Instruction Manual," issued by Hitachi Koki Co., Ltd., Shinagawa Intercity Tower A, 15-1, Konan 2-chome, Minato-ku, Tokyo 108-6020, Japan; pp. 1-30, 88, 90, and 92; 33 pages.

Two (2) Images of Laserkerf Model 125; Laserkerf, 669 Burton Pike, Georgetown, KY 40324; www.laserkerf.com; 2 pages.

Four (4) Images of Hitachi Model C10FSH—255mm (10") Slide Compound Saw with Laser Marker; Hitachi Koki Co., Ltd., Shinagawa Intercity Tower A, 15-1, Konan 2-chome, Minato-ku, Tokyo 108-6020, Japan; http://www.hitachi-koki.com/powertools/products/cutter/c10fsh/c10fsh.html; 5 pages.

One (1) Image of Hitachi Model C10FCH—255mm (10") Slide Compound Saw; Hitachi Koki Co., Ltd., Shinagawa Intercity Tower A, 15-1, Konan 2-chome, Minato-ku, Tokyo 108-6020, Japan; http://www.hitachi-koki.com/powertools/products/cutter/c10fce/c10fce.html; 1 page.

One (1) Image ofCraftsman Model21206-Craftsman Professional Laser Trac™ 12 in. Sliding Compound Miter Saw; Sears Holding Corporation, 3333 Beverly Road, Hoffman Estates, IL 60179; http://www.sears.com/sr/javasr/product.do?BV_UseBVCookie=Yes&verticle=TOOL&fromAuto=YES&bidsite=CRAFT&pid=00921206000; 1 page.

One (1) Image of Craftsman Model 28060—Craftsman 15 amp Circular Saw with Laser Trac™ Laser Guide; Sears Holding Corporation, 3333 Beverly Road, Hoffman Estates, IL 60179; http://www.sears.com/sr/javasr/product.do?BV_UseBVCookie=Yes&vertical=TOOL&pid=00928060000; 1 page.

Five (5) Image of Craftsman Model 21209—Craftsman 10 in. Compound Miter Saw with LaserTrac™; Sears Holding Corporation, 3333 Beverly Road, Hoffman Estates, IL 60179; http://www.sears.com/sr/javasr/product.do?BV_UseBVCookie=Yes&vertical=TOOL&pid=00921209000&tab=des#tablink; 1 page.

Two (2) Images of GMC Model LMS305—305mm Compound Mitre Saw with REDEYE® Laser Line Generator; Global Machinery Company; 45-55 South Centre Road, Melbourne Airport, Victoria 3045, Australia; http://203.89.231.185/index.cfm?ppage=products&pproduct_uuid=B695359F-AB36-4219-AB89F2C2FE9B78B8; 3 pages.

Two (2) Images of Rockwell Model RW2115L—7¼ " Laser Circular Saw; Rockwell Tools; 866-748-6657; http://www.rockwelltools.com/pages/1/index.htm; 3 pages.

EP Search Report for Aplication No. 05021582.1-2316.

* cited by examiner

GAUGE FOR USE WITH POWER TOOLS

FIELD OF THE INVENTION

The present invention generally relates to the field of power tools, and particularly to a gauge for determining structural factors of a workpiece to be operated upon by a power tool.

BACKGROUND OF THE INVENTION

The use of power tools is commonplace in numerous locations, from construction work sites to home work shops these devices are employed to accomplish myriad tasks. These power tool devices are further used to perform their functions on a variety of different workpieces, such as wood, metal, plastic, and the like.

Power tools may operate upon different workpieces, which may have different structural factors which may affect the task being performed. Many factors may contribute to the structural makeup of a workpiece. For instance, in a piece of wood the hardness, thickness, and the moisture content of the wood comprise structural factors.

Unfortunately, the power tools being employed currently may not include the capability of providing a measure of these different structural factors and account for these factors in determining operation of the power tool. This may contribute to the inefficient operation of the power tool which may result in decreased productivity. Further, failure to account for structural factors may contribute to a reduced life span of useful operation of the power tool due to increased operational stresses being placed upon the tool which may result in increased wearing of the working parts of the tool.

Therefore, it would be desirable to provide a device which enables the user of a power tool to determine the operational settings of the power tool based on determined structural factors of a workpiece to be operated upon by the power tool.

SUMMARY OF THE INVENTION

Accordingly, the present invention provides a gauge for coupling with a power tool. The gauge provides a system for determining structural factors of a workpiece to be operated upon by the power tool. For instance, the gauge may determine the hardness of a piece of wood which is to be cut by a saw or have a fastener, such as a nail or staple, driven into by a pneumatic fastener device, such as a nail gun or staple gun. In addition or alternatively, the gauge may establish a moisture level of the wood workpiece. These determined factors are then provided to the user of the power tool so that the operational settings of the power tool may be adjusted to assist in providing increased efficiency in the operation of the power tool. The increased efficiency in operation of the power tool may increase the useful lifespan of the power tool thereby increasing the productivity enabled through use of the power tool.

It is an object of the present invention to provide a method for operating a power tool upon a workpiece. A gauge is positioned appropriately to engage with the workpiece in a desired location. Once positioned, the gauge is engaged against the workpiece and determines a structural factor (i.e., hardness, thickness, and/or moisture content) of the workpiece. The determined structural factor is utilized to establish the operational settings of the power tool. After the desired settings are established, the power tool is engaged upon the workpiece to accomplish the function of the power tool.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Figure 1:
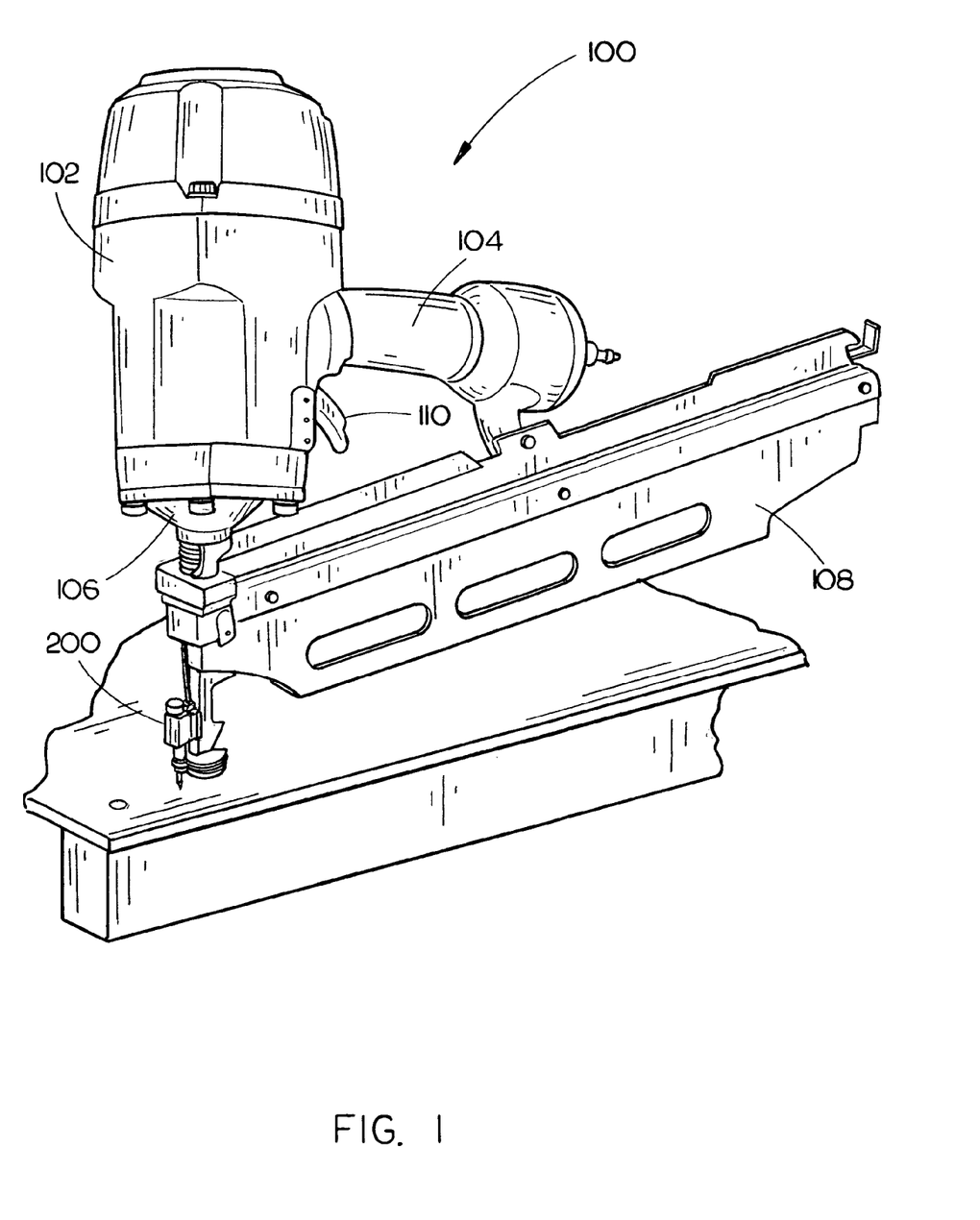
FIG. 1 is an illustration of a nail gun employing a gauge in accordance with an exemplary embodiment of the present invention.
Figure 2:
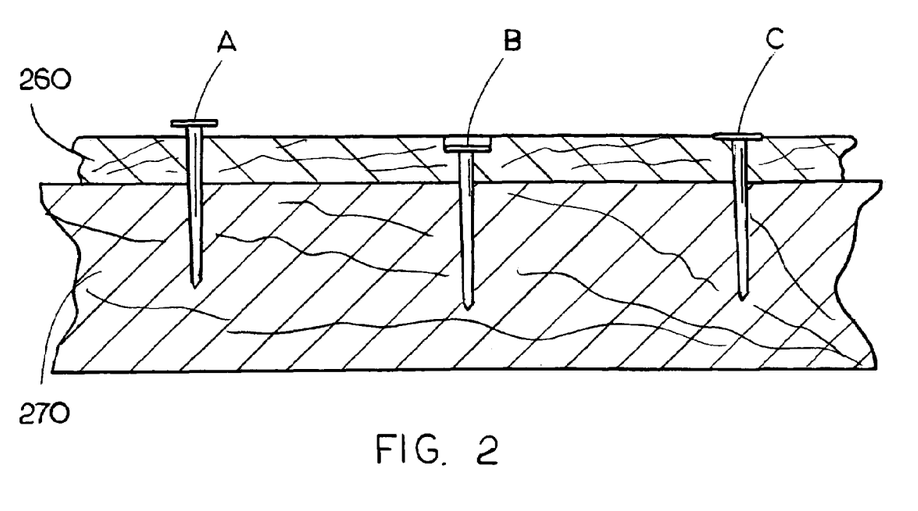
FIG. 2 illustrates various nails driven various depths to secure two workpieces.
Figure 3:
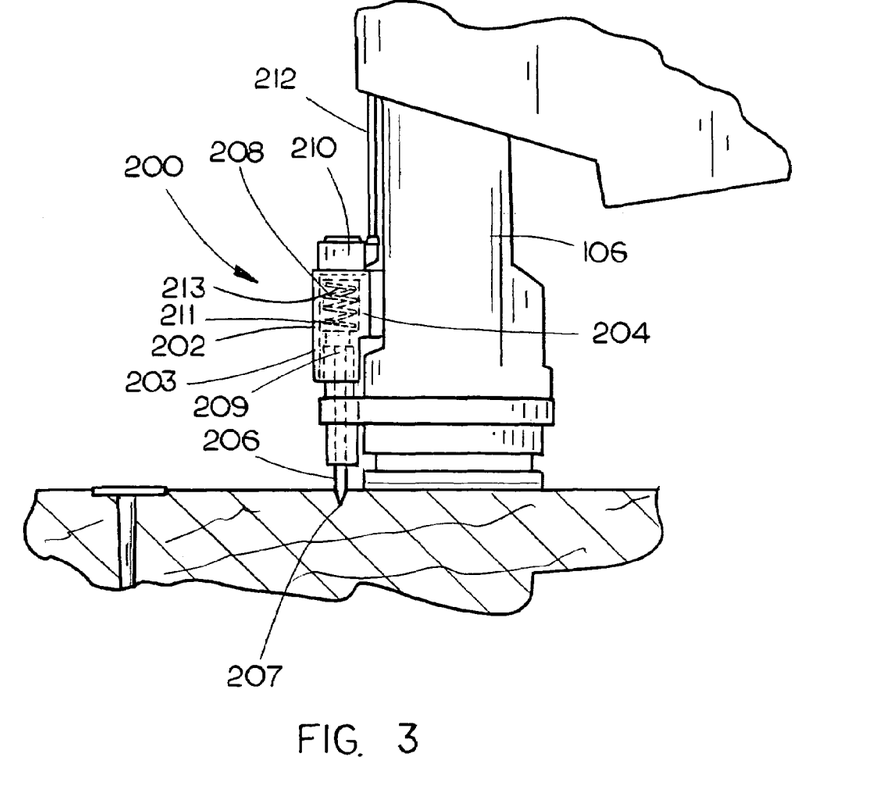
FIG. 3 is a side view illustration of the gauge connected with the nail gun wherein a probe is engaging with a workpiece.

Referring now to FIGS. 1 through 3, a pneumatic nail gun 100 including a gauge 200 is shown. It is contemplated that the gauge of the present invention may be employed with various devices, such as a stapler, and/or with variously enabled devices, such as a combustion nail gun, pneumatic stapler, combustion stapler, and the like. The nail gun 100 including a casing 102 integrally connected with a handle 104. The casing 102 is further connected with a nose casting 106. The nose casting 106 is connected with a nail loading assembly 108, the nail loading assembly is further connected with a handle 104. The nail loading assembly provides a nail which is operated upon by the nail gun 100. It is to be understood that the nail loading assembly may be variously configured as contemplated by those of ordinary skill in the art without departing from the scope and spirit of the present invention. A nail driving assembly includes a trigger 110 which is operationally connected, via a driver mechanism, with a driver blade. The driver mechanism provides a force for driving the driver blade through the nose casting 106 in order to drive the nail presented into the nose casting 106 from the nail loading assembly 108.

The gauge 200 includes a gauge housing 202 which may be mounted upon or connected with the nose casting 106. In the current embodiment, the gauge housing 202 further includes a mount 204 which allows for the connection of the gauge housing 202 with the nose casting 106. Further, the connection of the gauge 200 with the nose casting 106 is proximal to the end of the nose casting 106 which contacts a work surface, opposite the connection of the nose casting 106 with the casing 102 of the nail gun 100. It is contemplated that the nose casting 106 may include a mount member which allows for the connection of the gauge 200. Alternatively, the nose casting 106 may include various mounting devices for connecting with the gauge 200. For instance, a first mount device disposed on the nose casting 106 may connect with the mount 204 of the gauge 200 and a second mount device disposed on the nose casting 106 may provide a connection with the gauge housing 202 in a secondary location, alternative to the location of the mount 204.

The gauge 200 further includes a sensor assembly which includes a probe 206 that extends, at least partially, within the gauge housing 202. The probe has a first end 207 which extends from the gauge housing 202 to the outside environment. The probe 206 further includes a second end 209 which is disposed within the gauge housing 202 and connects with a first end 211 of a spring 208, the spring 208 being disposed within the gauge housing 202. The first end 207 of the probe 206 contacts a workpiece for determining at least one structural factor (i.e., hardness, thickness, moisture content) of the workpiece. The first end 211 of the spring 208 connects with the probe 206 and the second end 213 is connected to a sensor 210. The sensor assembly provides a measure of a structural factor (i.e., hardness, thickness, moisture content, and the like) of the workpiece for use in determining the operational settings of the nail gun 100 in the current embodiment. The determination of these structural factors allows the nail gun to be adjusted in terms of the force applied in driving the nail within the workpiece.

In operation, the forces encountered by the first end 207 of the probe 206 are translated through the second end 209 of the probe 206 to the first end 211 of the spring 208. The force exerted upon the spring 208 is translated through the second end 213 of the spring to the sensor 210. The sensor 210, via a connection by a linkage 212 with the nail driving assembly disposed internally within the casing 102 of the nail gun, translates information regarding the forces encountered by the first end 207 of the probe 206 to the nail driving assembly.

The translated information from the sensor assembly to the nail driving assembly may be utilized for determining the operational settings needed for the proper use of the nail gun or may be utilized for establishing the operational settings of the nail gun. In a pneumatic nail gun the operational settings may be established by setting the size of the driving chamber, thus determining the amount of compressed air, which is to be utilized for the driving of a driver blade of the nail driving assembly. Thus, the present invention, if it determines that the workpiece is relatively hard, may have that information translated through the sensor assembly to the nail driving assembly. The nail driving assembly may then automatically set the compressed air pressure to be utilized. Thus, the user may then fire the nail gun and will be utilizing that amount of force as indicated by the hardness factor determined by the gauge. If the nail gun were a combustion nail gun, the nail driving assembly may automatically set the size of the combustion chamber based on the structural factor information received from the sensor assembly.

As shown in FIG. 2, three variously driven nails "A", "B", and "C" are shown. Nail "A" is an underdriven nail, where the nail is shown driven into a workpiece 260 leaving at least a part of the nail shank exposed (raised above the surface of the workpiece 260) and therefore having a nail head in a position which is not planar with the surface of the workpiece 260. Nail "B" is an overdriven nail, where the nail is shown driven into the workpiece 260 with a nail head driven below the planar surface of the workpiece 260. Nails "A" and "B" are examples of improperly driven nails. In each instance, the nail has been driven to a depth which reduces the effectiveness of the nail in connecting the workpiece 260 with a secondary workpiece 270. In the case of nail "A", the nail shank is not being fully utilized for connecting the workpieces, while in the case of nail "B" the nail has weakened the connection by driving through a part of the workpiece 260. It may be the case that in the operation of a nail gun, such as nail gun 100, due to various structural factors of the workpiece(s) the nails may be underdriven or overdriven because the force settings of the nail driving assembly of the nail gun are not properly set. The force settings may be improperly set for various reasons, including an unawareness of structural factors of the workpiece(s), such as the hardness of the workpiece(s), which may require a higher force setting, and/or the moisture content of the workpiece(s), which may require a lower force setting. Nail "C" is an example of a properly driven nail wherein the nail shank is fully engauged with both the workpiece 260 and the secondary workpiece 270 and the nail head is driven to a planar position with the surface of the workpiece 260. In this example, the force setting of the nail driving assembly of the nail gun was properly set with respect to the structural factors of the workpiece(s). The present invention provides a method and apparatus which assists in providing a predetermination of structural factors of a workpiece(s) which may then allow the user of a nail gun to establish the proper force settings or allow the nail driving assembly to automatically establish the proper force settings for the nail driving assembly.

Figure 4A:
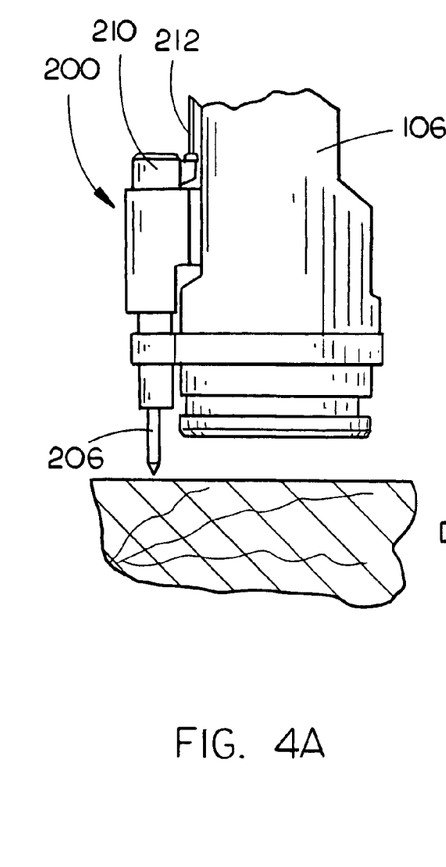
FIG. 4A is a side view illustration of the gauge connected with the nail gun wherein the probe is being initially positioned relative to the workpiece.
Figure 4B:
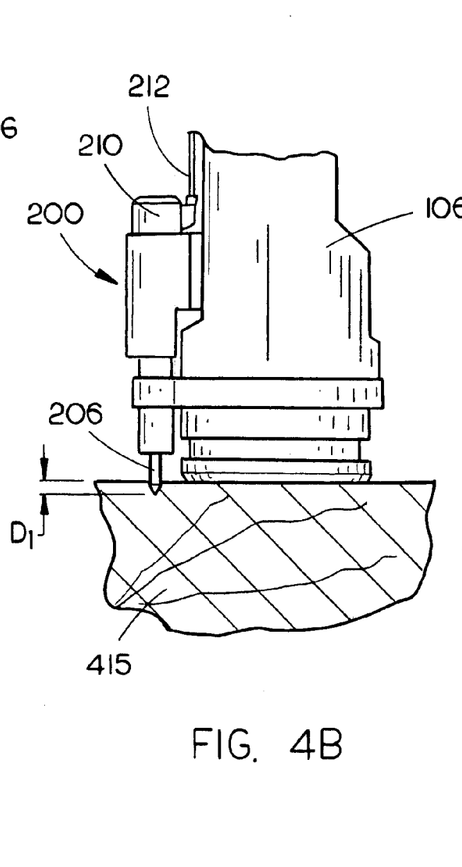
FIG. 4B is a side view illustration of the gauge connected with the nail gun wherein the probe is engaged with the workpiece and is providing a depth reading.
Figure 4C:
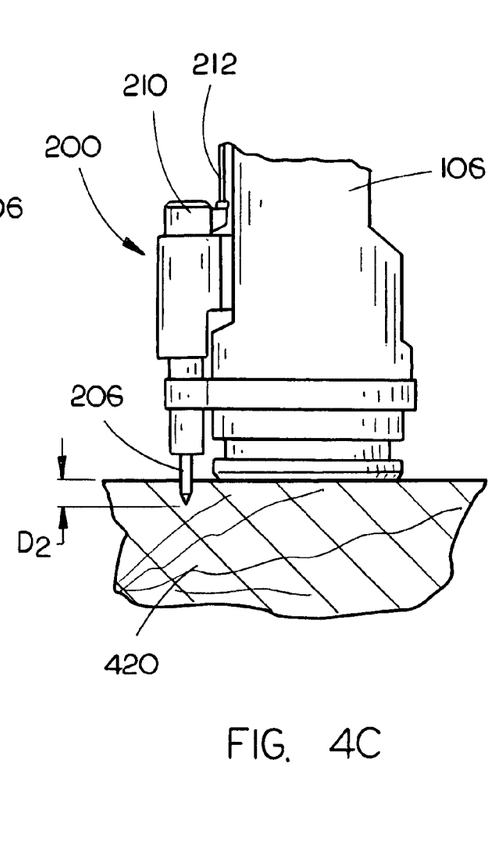
FIG. 4C is a side view illustration of the gauge connected with the nail gun wherein the probe is engaged with a workpiece and is providing a depth reading.

Referring now to FIGS. 4A, 4B and 4C, the engagement of the gauge 200, more particularly the probe 206 of the sensor assembly, against a workpiece is shown. In FIG. 4A, it is seen that the first end 207 of the probe 206 extends below the plane established by the end of the nose casting 106 which contacts against a workpiece. As the probe 206 contacts the workpiece it is retracted, in proportion to a structural factor of the workpiece, within the gauge housing 202 applying a force against the spring 208. The spring 208 is compressed within the gauge housing 202. In FIG. 4B, the probe 206 is contacted against a workpiece 415 and the probe 206 extends a distance "D1" into the workpiece 415.

The depth of penetration of the probe 206 within the workpiece 415 provides a force which is translated through the probe 206 to the spring 208 and ultimately the sensor 210. The sensor 210 provides information which indicates a specific hardness of the workpiece and or the moisture content of the workpiece based on the translated force. The sensor 210 then transmits this information via the linkage 212 to the nail driving assembly where it may be used to set the operational settings of the nail gun.

In FIG. 4C, the probe 206 contacts a second workpiece 420 and penetrates to a second distance "D2". In the current embodiment, the second distance "D2" corresponds to a greater penetration of the probe 206 into the workpiece 420 than is shown by distance "D1". This greater penetration may indicate numerous structural factors, such as a softer workpiece or a higher moisture content within the workpiece. The compression experienced by the spring 208 may be reduced, due to the greater penetration of the probe 206, which may result in the sensor 210 receiving a reduced translated force. Thus, the sensor 210, via linkage 212, may indicate that a reduced driving force is required which may be set by the user or by the nail driving assembly, as previously described.

The distance shown in FIG. 4A, that the probe 206 extends below the plane or surface of the end of nose casting 106 may vary as contemplated by those of ordinary skill in the art to provide an optimum sensor reading capability to the sensor assembly. In a preferred embodiment, the distance the probe 206 extends may be one to two centimeters. It is contemplated however that shorter distances or greater distances may be utilized for the present invention.

The mounting of the gauge housing 202 to the end of the nose casting 106 is via mount 204. The mount 204 may allow for the connection through the use of various fasteners such as screws, bolts, clips, probe and the like, which will secure the connection of the gauge housing 202 against the nose casting 106. It is contemplated that the nose casting 106 further includes a nose casting mount for connecting with the mount 204 of the gauge housing 202. The nose casting mount or the nose casting itself may include receivers, the number of receivers corresponding to the number of fasteners that may be used to mount the gauge housing 202. It is further contemplated that various mechanical connection assemblies or mechanisms may be utilized to connect the gauge housing 202 with the nose casting 106. For example, a snap fit mechanism may be used to mount the gauge housing 202 to the nose casting 106. Alternative mechanisms such as compression lock mechanisms, latch lock mechanisms, and spring loaded lock mechanisms may be utilized for connecting the gauge housing 202 with the nose casting 106. It is further contemplated that the gauge housing 202 may be integrally connected with the nose casting 106. The integral connection may be established utilizing various construction techniques for the nose casting, welding techniques and/or through the use of various adhesives; such as epoxy compounds, cement adhesives, and the like. The integral connection may provide improved structural integrity of the connection between the gauge housing 202 and the nose casting 106. However, it is contemplated that the various connection mechanisms and fasteners may establish the connection of the gauge housing 202 with nose casting 106, in a sufficiently rigid manner enabling the proper operation of the sensor assembly within the gauge housing 202.

The probe 206 is of a sufficient length to a least partially extend a distance from the gauge housing 202 beneath the plane of the bottom of the nose casting 106. As mentioned previously, the overall length of the probe 206 may vary to provide for the operation of the sensor assembly. In a preferred embodiment, the probe 206 is composed of steel. Alternative materials such as composite material, various metals, wood, and the like may be used to construct the probe 206 of the present invention.

The spring 208 is a compression spring of a sufficient length to connect with the probe 206 and the sensor 210. The spring 208 is a steel compression spring. Alternatively, various metals, composite materials, and the like may be utilized to provide spring 208 with various tensile strengths (spring force). These tensile strengths may be utilized for providing the probe 206 with predetermined resistance factor. The predetermined resistance factor may be set for use based on the various materials with which the nail gun is to be employed. For example, when used primarily for driving nails into framing materials which may comprise a specific type of wood, certain structural hardness factors may be taken into account when selecting the tensile strength of the spring. Therefore, the spring may be preferably optimized for operation with various specific materials. The length of the spring 208 may vary depending on various factors including the size of the gauge housing 202 and the distance between the probe 206 and the sensor 210.

The sensor 210 connects with the second end 213 of the spring 208 and provides for the determination of the structural factor based on the translated force received via the probe 206 engaging with a workpiece. In the preferred embodiment, the sensor 210 is a pressure plate, the pressure plate reacting or being activated by pressure exerted upon it through compression of the spring 208 via engagement against probe 206. It is contemplated various alternative sensor technologies may be employed without departing from the scope and spirit of the present invention. For instance, the sensor 210 may be a sliding scale device, whereby a sliding member may be moved by the force exerted through the spring 208. The sliding member provides a determination of structural factors based on the position it is placed into by engagement with the spring 208.

The linkage 212 provides for the communication between the sensor 210 and the nail driving assembly disposed within the casing 102 of the nail gun 100. The communication including information relating to the measurement of the structural factor of the workpiece as indicated by the sensor 210 readings. The information may be transmitted in various ways as contemplated by those of ordinary skill in the art. For example, the information provided by the sensor 210 may be directly transmitted via a mechanical linkage assembly to the nail driving assembly, wherein the mechanical linkage assembly provides for setting the correct operational force settings of the nail driving assembly. For example, the mechanical linkage may connect with the driving chamber of the pneumatic nail gun 100 and set the size of the driving chamber based on the information received from the sensor assembly. In the alternative, the linkage may be an electrical communication pathway, providing the information to various devices included within the nail gun 100 which allow for the proper force settings of the nail driving assembly to be made. For example, the electrical linkage may connect with a trigger device of the nail gun and control the movement of the trigger device which may translate into control over the amount of compressed air allowed into the driving chamber. It is contemplated that the linkage 212 may provide a connection utilizing various technologies but allowing for the control of the of the operational settings of the nail gun.

In the example where the linkage provides an electrical communication pathway, the nail gun 100 may be further disposed with a user interface. The user interface providing a read-out or display of information gathered from the sensor 210 of the sensor assembly. The user interface allowing the user to visually ascertain the readout information and then provide for the adjustment of the operational force settings of the nail driving assembly of the nail gun 100 to proper operational force settings based on the readout information. The adjustments to the operational force settings may be made automatically by a communicative connection between the user interface and the nail driving assembly of the nail gun. In an alternative embodiment, the user interface may simply be a readout display and the user may then take that information and manually adjust the operational force settings of the nail driving assembly of the nail gun 100 based on the readout information.

The gauge housing 202 may be composed of various materials. In the preferred embodiment, the gauge housing 202 is composed of a steel material. In alternative embodiments gauge housing 202 may be composed of various composite materials, metals, and the like, which provide sufficient structural integrity and rigidity for proper operation of the gauge 200. It is contemplated that the gauge housing 202 may determine the size of the spring 208 to be utilized by the dimensions of an interior cavity 203 of the gauge housing 202. For example, a reduced size interior cavity 203 may require the use of a small spring, an increase in the size of the interior cavity 203 may allow for the use of a larger spring which may provide more play and sensitivity to the sensor assembly. It is contemplated that the internal cavity 203 may be one long continuous cavity, running the length of the housing.

In the alternative, the interior cavity 203 may be established as several cavity sections, or multiple cavity sections. These multiple cavity sections may define different internal diameters. These different internal diameters may allow for proper operation of the gauge 200. For example, a first internal cavity section may have a first inner diameter to accommodate the compression spring 208. A first internal cavity may extend a partial distance down the housing and connect with a second internal cavity. The second internal cavity, being of a sufficient size to allow for the operation of the probe 206 to partially extend through a second internal cavity and engage with the compression spring 208 on the one end and then extend to the outside of the gauge housing 202 for engagement of the probe 206 against the work surface.

It is further contemplated that the gauge housing 602 may include an indicator assembly for indicating the proper operational settings of the nail gun 100 as determined by the identified structural factors of the workpiece. The indicator assembly may be a display which provides a visually ascertainable readout of information. For example, the indicator assembly may include index markers disposed upon the gauge housing, the index markers indicating an operational setting for the nail gun. The index markers may be visually aligned with the second end of the probe when the probe is contacted against a workpiece, thereby, providing an indication of the proper operational settings for the nail gun with respect to the workpiece. Alternatively, the indicator assembly may be an indexing system whereby a pointer correspondingly identifies one of a series of operational setting parameters which correlates with the determined structural factors.

Figure 5:
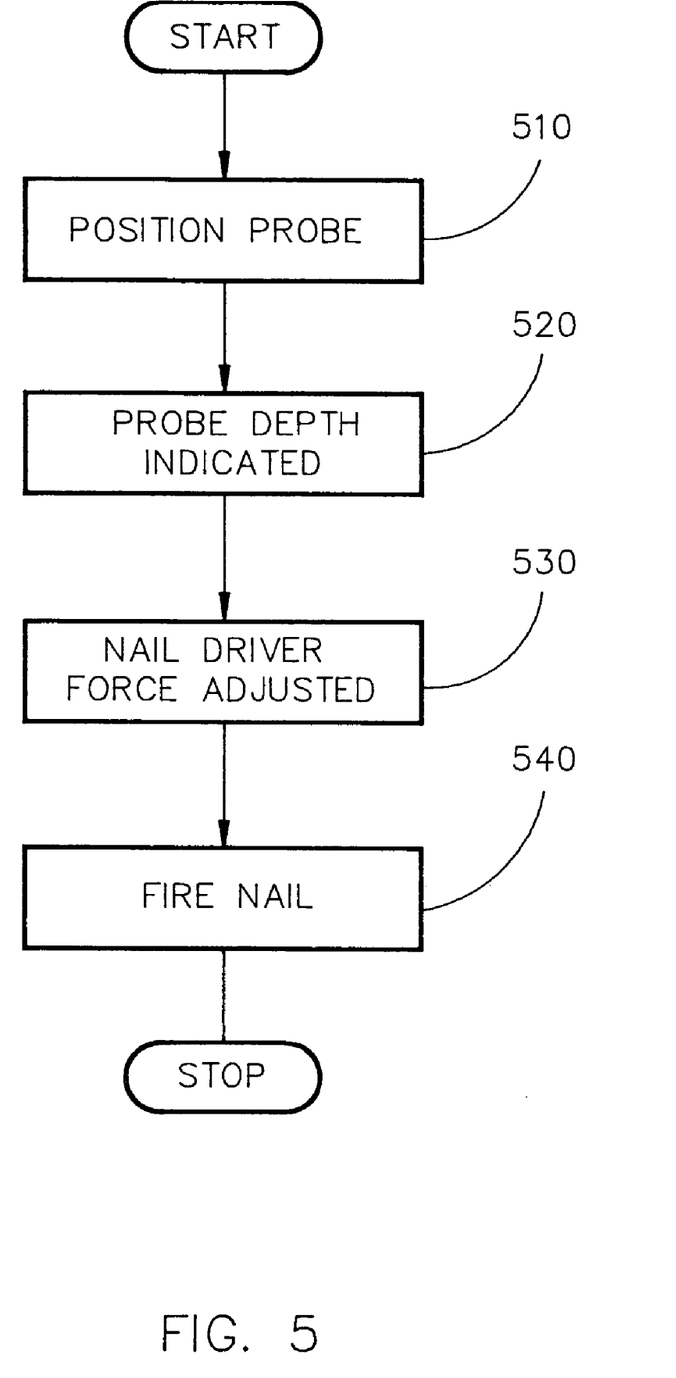
FIG. 5 illustrates a method of operating the nail gun employing the gauge in accordance with an exemplary embodiment of the present invention.

Referring now to FIG. 5, a method of operating the nail gun 100 is illustrated. In a first step, the probe of the sensor assembly is positioned. It is to be understood that the method of operation described herein is equally applicable for the use of various types of devices, such as staple guns, utilizing various operational capabilities, such as a pneumatic gun, combustion gun, and the like. After the first step 510, the probe is engaged with the workpiece and in step 520 the depth that the probe extends within the workpiece is indicated. The depth the probe extends into the workpiece providing a measure of a structural factor(s) of the workpiece. In step 530, the force setting for the nail driver is adjusted to correspond with the information regarding the structural factor(s) of the workpiece. For example, the size of the driving chamber may be adjusted to provide a particular amount of driving force to the driver blade of the nail driving assembly. In a final step 540, the nail gun is fired and the nail is driven in accordance with the proper operational force settings as determined through use of the probe.

The method of the current invention further contemplates an additional step of the probe depth being indicated by a user interface communicatively linked with the probe. The user interface may provide the capability for making the necessary force setting adjustment for the driving of the nail itself or the user interface may simply provide a readout of the information allowing for the manual adjustment of the force setting by the user.

In the alternative, a method of operating a power tool is contemplated. In a first step the probe of the sensor assembly of the gauge is positioned for engaging against a workpiece. The power tool being positioned to operate upon the workpiece. With the probe engauged against the workpiece, a probe depth is indicated. The probe depth being a distance the probe penetrates within the workpiece, see FIGS. 4B and 4C as examples of the penetration of the probe within the workpiece. Utilizing the indicated probe depth, the operational settings of the power tool are determined. The operational settings corresponding to the probe depth, which is an indication of a structural factor of the workpiece. After the proper operational settings are made the power tool is engauged with the workpiece performing its function upon the workpiece. It is further contemplated that various other component features and capabilities may be employed, such as the use of a user interface device, non-contact measurement and alignment system, and the like to assist in making the structural factor determination or increase the ease of use of the present invention, without departing from the scope and spirit of the present invention.

Referring generally now to FIGS. 6 through 9, a saw assembly 600 connected with a gauge 700 and a non-contact measurement system 800, is shown. The saw assembly 600 is a standard miter saw constructed with a motor 602 operatively connected to a saw blade 604. It is contemplated that the saw assembly may vary, such as a sliding miter saw, compound saw, table saw, and the like. Connected to a mount mechanism 603 and about the saw blade 604 is a cover 606 (upper blade guard). A handle 608 is connected with the motor 602 and cover 606. The mount mechanism 603 adjustably connects a base 610 with the cover 606, motor 602, and saw blade 604. In the current embodiment, the mount 603 includes a first arm connected on a first end with the base 610 and adjustably connected on a second end with a first end of a second arm. The second end of the second arm being connected with the cover 606. The base 610 further provides a seat for a workpiece to be operated upon by the saw blade 604.

Figure 6:
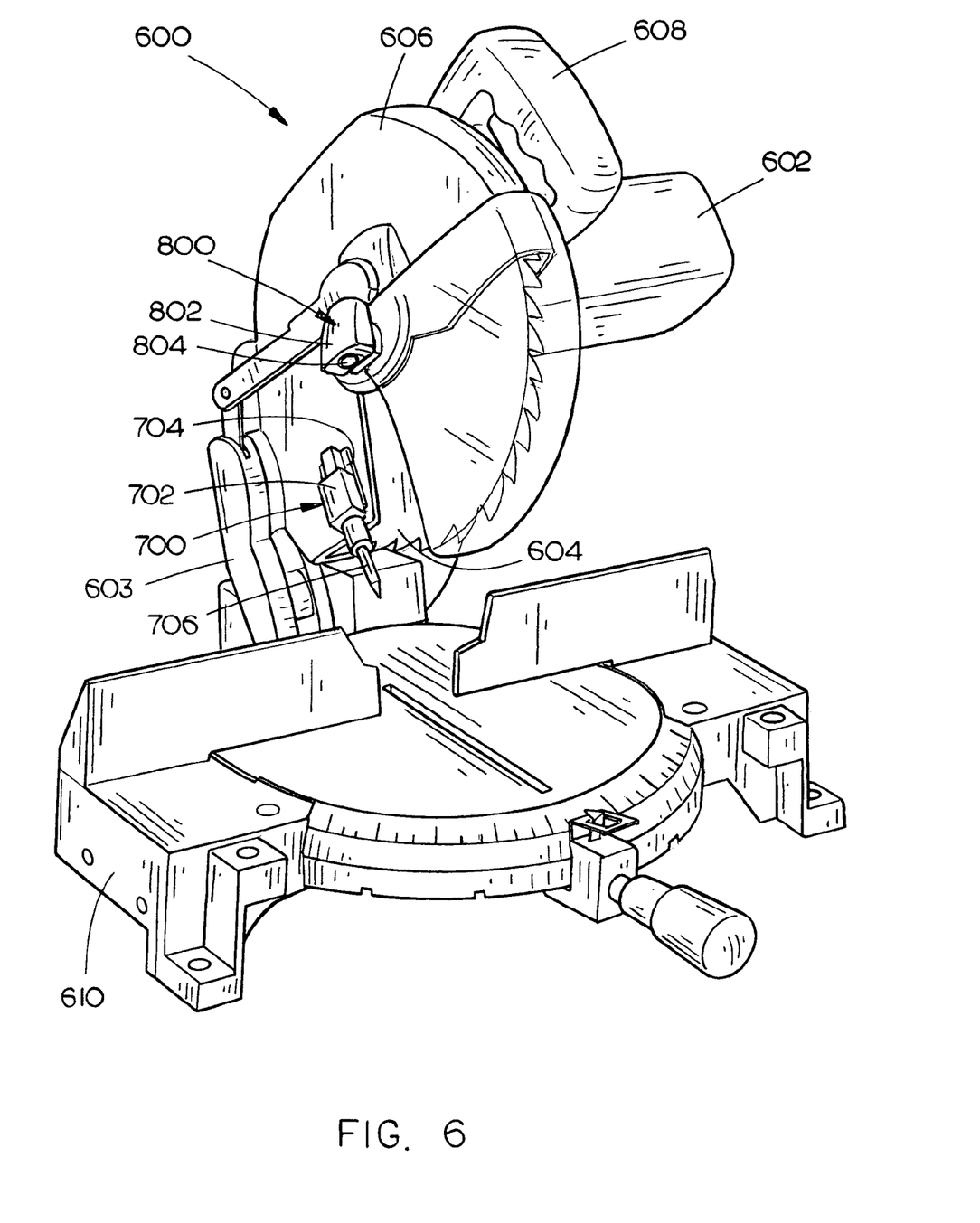
FIG. 6 is an illustration of a miter saw employing a gauge and a non-contact measurement apparatus in accordance with an exemplary embodiment of the present invention.

The gauge 700 includes a gauge housing 702 which connects to the cover 606 via a mount 704, a sensor assembly is disposed within the gauge housing 702 and includes a probe 706 connected to a spring 708. The spring 708 is further connected to a sensor 710. The gauge 700 is similar in all respects to the gauge 200 described previously, except that the mount 704 allows the gauge housing 702 to move, in a sliding manner. Therefore the mount 704 allows for the adjusting of the position of the gauge housing 702 relative to the cover 606. The gauge 700 is disposed upon or connected with the cover 606 in a location which allows the gauge to contact a workpiece when the workpiece is seated upon the base 610 and allow for the gauge 700 via the sensor assembly to determine at least one structural factor (i.e., hardness, moisture content, and the like) of the workpiece. The structural factor determination providing an indication of the correct operational settings for the saw assembly 600. The operational settings may include initial saw blade speed, running saw blade speed, cut through saw blade speed, saw blade teeth configuration, size of saw blade, and the like which may assist in increasing the efficiency of cutting performed by the saw blade 604 of the saw assembly 600.

Figure 7:
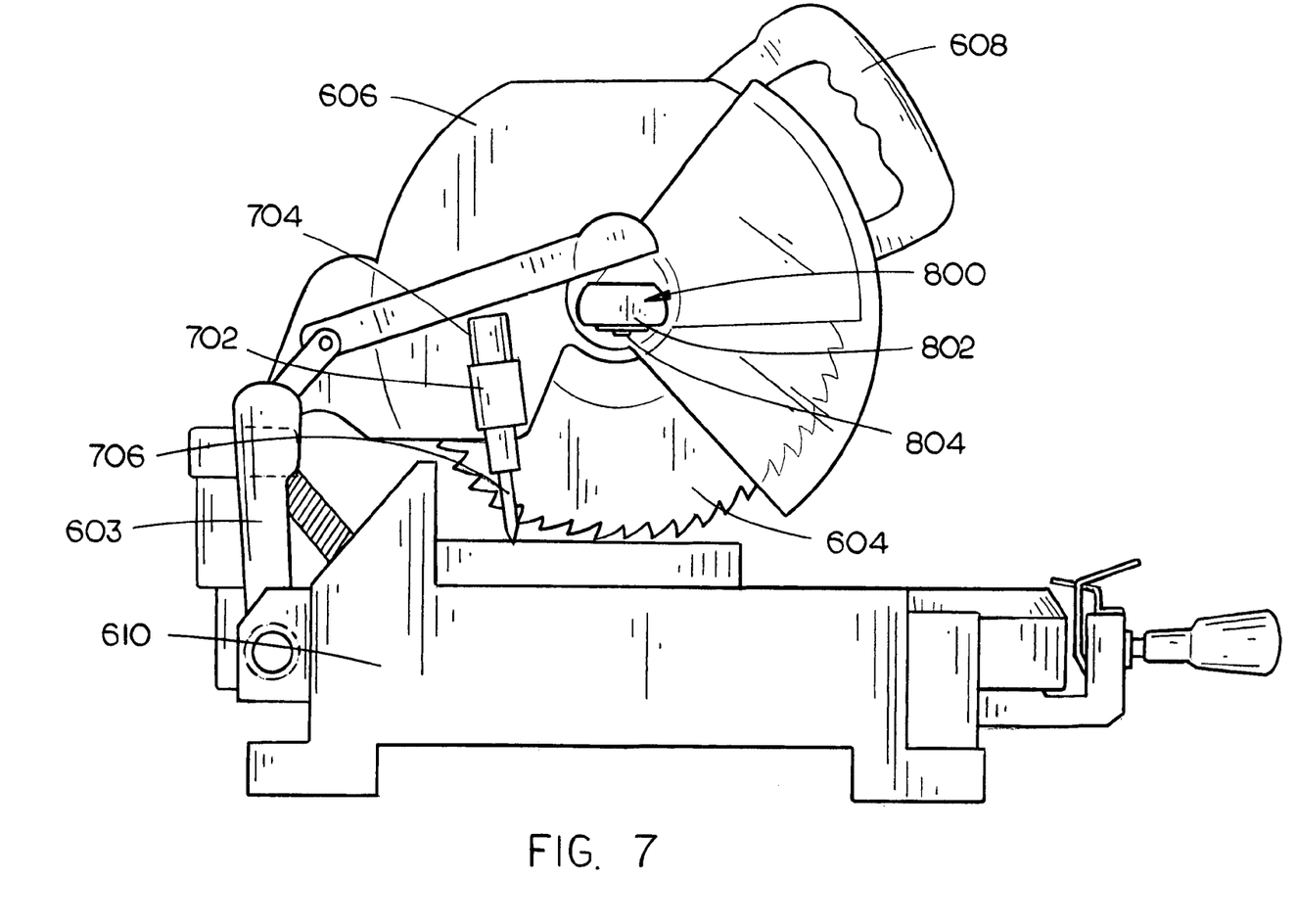
FIG. 7 is a side view illustrating a probe of the gauge contacting a workpiece disposed on a frame of the miter saw.

As shown in FIG. 7, the probe engages against the surface of the workpiece and depending upon the depth of penetration of the probe applies a compressive force to the spring 708. A linkage, similar to linkage 212 described previously, may be utilized for transmitting data/information from the gauge 700 to the saw assembly 600. As discussed previously with respect to the nail gun 100, the saw assembly 600 may further include a user interface which is communicatively coupled via a linkage to the gauge 700. The user interface may provide a readout display of the structural factors detected by the engagement of the probe against the workpiece.

It is further contemplated that the gauge housing 702 may include an indicator assembly for indicating the proper operational settings of the saw assembly 600 as determined by the identified structural factors of the workpiece. The indicator assembly may be a display which provides a visually ascertainable readout of information. Alternatively, the indicator assembly may be an indexing system whereby a pointer correspondingly identifies one of a series of operational setting parameters which correlates with the determined structural factors.

Figure 8:
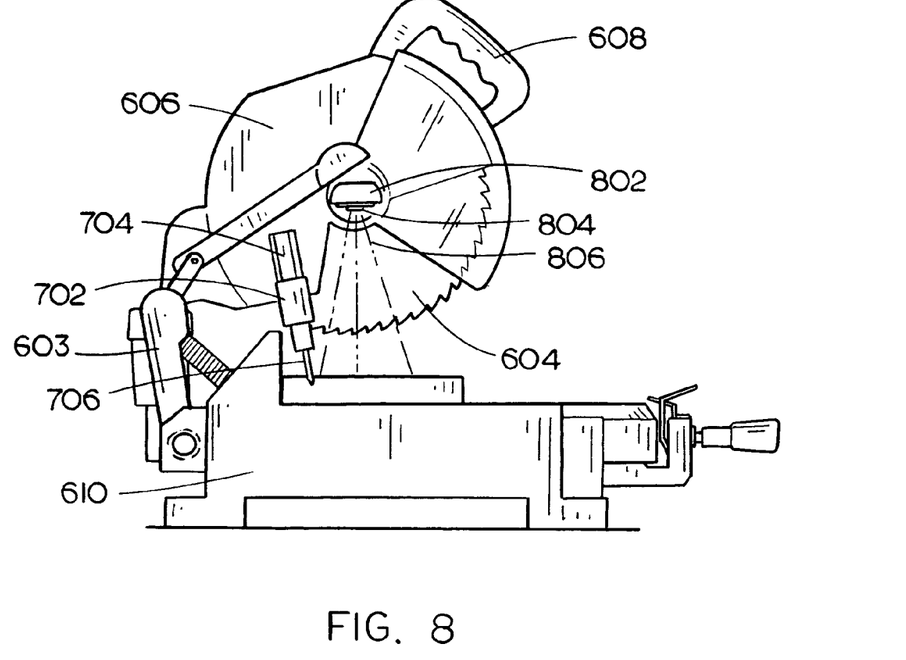
FIG. 8 is a side view illustrating the probe engauge with the workpiece and the non-contact measurement apparatus establishing a workpiece thickness measurement.
Figure 9:
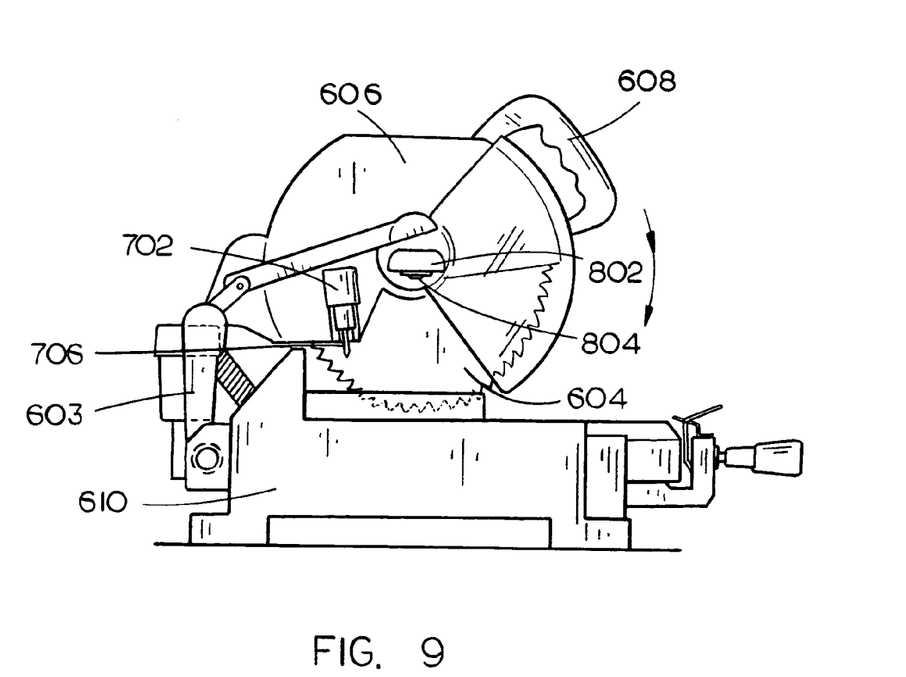
FIG. 9 is a side view illustration of a saw blade of the miter saw engauged with the workpiece after the gauge and non-contact measurement apparatus have completed their readings.

As seen in FIGS. 8 and 9, the gauge housing 702 including the sensor assembly may engauge with a workpiece to determine at least one structural factor and then be slidably repositioned to avoid contact by the sensor assembly with the workpiece as the workpiece is being cut by saw blade 604. This may reduce the risk of any inadvertent contact occurring to the gauge 700 during operation of the saw assembly 600. It is contemplated that various mechanical connection mechanisms may be employed to provide the adjustable connection of the gauge 700 with the saw assembly 600. For example, a rack and pinion system, including an adjustment knob connected to the pinion for engagement by a user, may be utilized. In operation, the rotation of the adjustment knob by the user may cause the pinion to travel along the rack. The direction of travel may be determined by the user through the direction of rotation applied to the adjustment knob.

Alternatively, the adjustment of the gauge housing 702 along the mount 704 may occur automatically. For instance, a user interface device may be communicatively linked with the gauge 700 including a powered mechanical adjustment system. The user may select the type of adjustment to be made upon the user interface. The adjustment command may then be transmitted to the powered mechanical adjustment system causing the powered mechanical adjustment system to execute the command. It is contemplated that various commands and power mechanical adjustment systems may be employed to provide an automatic adjustment capability to the gauge 700.

A non contact measurement and alignment system 800 includes a housing 802 mounted to the cover 606. In the alternative the housing 802 may be connected in various locations about the saw assembly 600. For example, the housing 802 may be positioned in various locations about the cover 606. Alternatively, the housing 802 may be mounted in various locations upon the saw assembly or the housing 802 may be remotely mounted from the saw assembly. Disposed within the housing 802 is a laser source, i.e. a laser generator. The laser source emitting a laser beam 806 through the lens to an environment outside of the housing 802. The non contact measurement and alignment system 800 further includes a detector which detects the striking of an incident laser beam emitted from the laser source, off various surfaces. The detector may detect laser light being reflected back from surfaces such as the base 610 or from a workpiece seated upon the base 610. It is contemplated that the detector is capable of detecting minute amounts of electromagnetic radiation from a laser beam.

Figure 10:
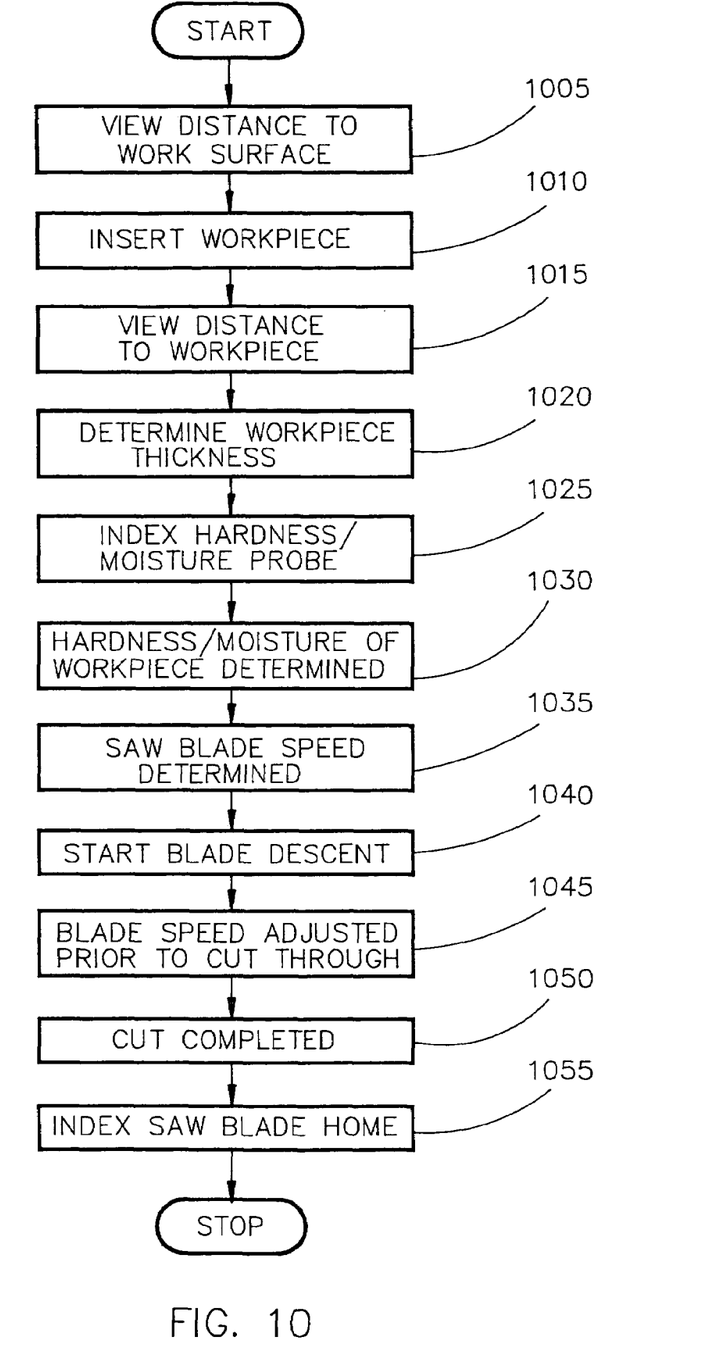
FIG. 10 is a method of operating the miter saw employing the gauge and non-contact measurement apparatus in accordance with an exemplary embodiment of the present invention.

Referring to FIG. 10, a method of operating a saw assembly, such as the saw assembly 600, is provided. In a first step 1005 a distance to a work surface is established. This measurement is provided as a function of the distance from the non-contact measurement and alignment system 800 to the seating surface provided by the base 610. In operation the laser beam 806 is emitted and strikes the base 610. The laser beam 806 is reflected from the base 610 and at least a portion of that reflected light is detected by the detector. After that distance is established in step 1010, a workpiece is inserted or seated upon the base 610 in a position to be operated upon by the saw blade 604. In step 1015, the distance to the workpiece is established utilizing a non contact measurement system. The laser beam 806 is emitted and provides a distance reading with respect to the workpiece seated upon the base 610. In step 1020, the thickness of the workpiece is determined by taking the original distance from the non contact measurement and alignment system 800 to the work surface and subtracting the second distance, which is the distance from the non contact measurement and alignment system 800 to the workpiece when placed upon the base 610 of the saw assembly 600.

In step 1025, the gauge is employed to determine at least one structural factor of the workpiece. For instance, the gauge may determine the hardness of the workpiece or moisture content of the workpiece. In step 1030, the hardness or moisture is determined. In step 1035, the saw blade speed is determined based on the determined structural factor, the hardness or moisture of the workpiece. In step 1040, the descent of the saw blade is begun in preparation for the cutting operation. In step 1045, the blade speed is adjusted prior to the cut through which may assist in increasing the useful lifespan of the saw blade. In step 1050, the cut is completed, then in step 1055, the saw blade is returned to its index/home position.

It is understood that the specific order or hierarchy of steps in the methods disclosed are examples of exemplary approaches. Based upon design preferences, it is understood that the specific order or hierarchy of steps in the method can be rearranged while remaining within the scope and spirit of the present invention. The accompanying method claims present elements of the various steps in a sample order, and are not necessarily meant to be limited to the specific order or hierarchy presented.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A gauge, for use with a power tool engaging a workpiece, comprising:
   a housing connected to the power tool;
   a sensor assembly disposed in the housing, the sensor assembly including a probe extending from the housing,
   wherein the probe is configured to determine a measure of a structural factor of the workpiece for use in determining an operational setting of the power tool prior to application of the power tool to the workpiece.

2. The gauge of claim 1, the sensor assembly further comprising:
   a spring connected to the probe;
   a sensor connected to the spring; and
   a linkage connected to the sensor.

3. The gauge of claim 1, further comprising a mount which connects the housing with the power tool.

4. The gauge of claim 1, wherein the housing is removable from the power tool.

5. The gauge of claim 1, further comprising a user interface for providing a readout of information.

6. The gauge of claim 1, further comprising a non-contact measurement and alignment system.

7. The gauge of claim 1, further comprising an adjustment system coupled to the sensor assembly and configured to adjust an operational setting of the tool in response to the measure of the structural parameter.

8. The gauge of claim 1, wherein the structural factor comprises hardness.

9. The gauge of claim 1, wherein the structural factor comprises thickness.

10. The gauge of claim 1, wherein the structural factor comprises moisture content.

11. The gauge of claim 1, wherein the probe is positioned on the power tool to penetrate the workpiece.

12. A gauge, for use with a power tool engaging a workpiece, comprising:
   a housing connected to the power tool;
   a probe including a first end extending from the housing a second end at least partially disposed within the housing;
   a spring including a first end and a second end, the first end connected with the second end of the probe and the second end connected to a sensor,
   wherein the probe connected via the spring to the sensor is configured to determine a measure of a structural factor of the workpiece for use in determining an operational setting of the power tool prior to application of the power tool to the workpiece.

13. The gauge of claim 12, further comprising a linkage connected to the sensor.

14. The gauge of claim 12, wherein the housing is removable from the power tool.

15. The gauge of claim 12, further comprising a user interface communicatively coupled with the sensor.

16. The gauge of claim 12, further comprising a non-contact measurement and alignment system connected to the power tool.

17. The gauge of claim 12, further comprising an adjustment system coupled to the sensor assembly and configured to adjust an operational setting of the tool in response to the measure of the structural parameter.

18. The gauge of claim 12, wherein the structural factor comprises at least one of hardness, thickness, and moisture content.

19. The gauge of claim 12, wherein the probe is positioned on the power tool to penetrate the workpiece.

20. A gauge, for use with a power tool engaging a workpiece, comprising:
   means for determining a structural factor of the workpiece prior to application of the power tool to the workpiece; and
   means for determining an operational setting of the power tool based on the means for determining the structural factor.

21. The gauge of claim 20, wherein the means for determining a structural factor comprises:
   a housing connected with the power tool;
   a probe including a first end extending from the housing and a second end at least partially disposed within the housing; and
   a spring including a first end and a second end, the first end connected with the second end of the probe and the second end connected to a sensor,
   wherein the probe connected via the spring to the sensor provide a measure of a structural factor of the workpiece for use in determining an operational setting of the power tool.

22. The gauge of claim 21, further comprising a mount for connecting the housing with the power tool.

23. The gauge of claim 21, wherein the housing is removable from the power tool.

24. The gauge of claim 21, further comprising a linkage for connecting with the sensor.

25. The gauge of claim 20, wherein the means for determining an operational setting of the power tool includes a user interface communicatively coupled with the means for determining a structural factor.

26. The gauge of claim 20, wherein the structural factor comprises at least one of hardness, thickness, and moisture content.

27. The gauge of claim 20, wherein the means for determining a structural factor of the workpiece is positioned on the power tool to penetrate the workpiece prior to application of the power tool to the workpiece.

* * * * *